United States Patent
Harris et al.

(10) Patent No.: US 7,582,752 B2
(45) Date of Patent: Sep. 1, 2009

(54) PROCESS FOR THE RESOLUTION OF NEFOPAM

(75) Inventors: Michael John Harris, Manchester (GB); Stuart Brown, Manchester (GB)

(73) Assignee: Sosei R&D Ltd., Essex (GB)

( * ) Notice: Subject to any disclaimer, the term of this patent is extended or adjusted under 35 U.S.C. 154(b) by 127 days.

(21) Appl. No.: 10/580,621

(22) PCT Filed: Dec. 13, 2004

(86) PCT No.: PCT/GB2004/005198

§ 371 (c)(1), (2), (4) Date: Mar. 27, 2007

(87) PCT Pub. No.: WO2005/056539

PCT Pub. Date: Jun. 23, 2005

(65) Prior Publication Data

US 2007/0276137 A1    Nov. 29, 2007

(30) Foreign Application Priority Data

Dec. 12, 2003 (GB) .................................. 0328871.9

(51) Int. Cl.
*C07D 487/00* (2006.01)
*C07D 491/00* (2006.01)
*C07D 513/00* (2006.01)

(52) U.S. Cl. ...................................................... 540/468

(58) Field of Classification Search ....................... None
See application file for complete search history.

(56) References Cited

U.S. PATENT DOCUMENTS 4,269,833 A * 5/1981 Treiber et al. ........... 514/211.01

FOREIGN PATENT DOCUMENTS

DE   1620198   *   4/1972
EP   0 970 935 A   1/2000

OTHER PUBLICATIONS

Blascke et al. Archiv der Pharmazie, 1987, 320(4), 341-7 (abstract).*

* cited by examiner

*Primary Examiner*—James O Wilson
*Assistant Examiner*—Noble Jarrell
(74) *Attorney, Agent, or Firm*—Saliwanchik, Lloyd & Saliwanchik

(57) ABSTRACT

A process for increasing the optical purity of a mixture of enantiomers of nefopam uses a substantially single enantiomer of a O,O-diaroyltartaric acid as a resolving agent, via a bisnefopam salt of the acid. This salt is new.

11 Claims, No Drawings

PROCESS FOR THE RESOLUTION OF NEFOPAM

This application is a National Stage Application of International Application No. PCT/GB2004/005198, filed Dec. 13, 2004; which claims priority to British Application No. 0328871.9, filed Dec. 12, 2003.

FIELD OF THE INVENTION

The present invention relates to a resolution process, for the manufacture of the single enantiomers of nefopam.

BACKGROUND OF THE INVENTION

Nefopam is a chiral drug that has been developed for the treatment of moderate to severe pain. Although nefopam is marketed as a racemic mixture, the enantiomers of the drug have been shown to exhibit different biological activities. In vitro and in vivo studies have shown that (+)-nefopam has more potent analgesic and dopamine, norepinephrine and serotonin-uptake inhibitory properties than (−)-nefopam. WO03/105832 discloses that nefopam has utility in the treatment of emesis and related conditions, with (+)-nefopam being the preferred enantiomer.

An efficient and reliable method for the preparation of the individual enantiomers of nefopam and nefopam analogues is desirable. As racemic nefopam is readily available, a classical resolution process, involving separation of diastereoisomeric salts by selective crystallisation may be suitable.

Blaschke et al, Arch. Pharm. (Weinheim) 320:341-347 (1987), discloses resolution of nefopam, using 1 molar equivalent of O,O-dibenzoyl-L-tartaric acid. The resolution proceeds via formation of the monotartrate salt.

SUMMARY OF THE INVENTION

This invention is based on the surprising discovery that racemic or non-racemic nefopam can be resolved more efficiently, using a substantially single enantiomer of O,O-dibenzoyltartaric acid or a related O,O-aroyltartaric acid as a resolving agent, via formation of a novel bisnefopam tartrate (nefopam hemitartrate) salt.

An advantage of the process of the present invention is that the resolving agent can be easily recovered in a state of high purity, such that it can be re-used in one or more subsequent resolution processes. Further, if desired, less than 1.0 molar equivalent of resolving agent may be used in the process.

DESCRIPTION OF THE INVENTION

The process of this invention may be carried out under conditions that are generally known to those skilled in the art of classical optical resolution methods.

In a typical experiment, nefopam was dissolved in ethanol then treated with a solution of O,O-dibenzoyl-L-tartaric acid monohydrate (1.0 mol equivalent). The resulting solution was allowed to stand until precipitation occurred. Collection of the solid and recrystallisation produced the (+)-bis-nefopam O,O-dibenzoyl-L-tartaric salt in 22% yield and 99% enantiomeric excess.

Since both enantiomers of, say, O,O-dibenzoyltartaric are readily available in quantity, either can be used to effect the resolution, depending on which enantiomer of nefopam is required. Thus, (−)-bis-nefopam O,O-dibenzoyl-D-tartaric salt may be prepared in a similar yield and optical purity, utilizing O,O-di-p-toluoyl-D-tartaric acid as the resolving agent.

The resolving agent may also be used to increase the optical purity of enantiomerically-enriched nefopam. Thus, when both enantiomers of nefopam are required, the processes described above can be compressed, one enantiomer being recovered by the resolution and the opposite enantiomer being extracted from the mother liquors of the resolution. In practice, when (+)-bis-nefopam O,O-dibenzoyl-L-tartaric salt is recovered as described above, the mother liquors remaining are processed to isolate nefopam free base enriched in the (−)-isomer, which is then purified by treatment with O,O-dibenzoyl-D-tartaric and crystallization of the resultant salt.

The yield of the resolution procedure can be improved by a reverse resolution process. Thus, when racemic nefopam is treated with O,O-di-p-toluoyl-D-tartaric acid, (−)-bis-nefopam O,O-dibenzoyl-D-tartaric salt is isolated. The mother liquors, now enriched with (+)-nefopam, can be resolved in the normal way, using O,O-dibenzoyl-L-tartaric acid, to give (+)-bis-nefopam O,O-dibenzoyl-L-tartaric salt, in good yield. The same reverse resolution process can be applied to the isolation of (−)-bis-nefopam O,O-dibenzoyl-L-tartaric salt, in good yield.

A substantially single enantiomer that is used in or produced by the process of the invention may be in at least 80% e.e., preferably at least 90% e.e., more preferably at least 95% e.e., and most preferably at least 98% e.e.

The present invention is illustrated by the following Examples.

EXAMPLE 1

Nefopam Free Base

Racemic nefopam hydrochloride (5.0 Kg, 17.2 mol) was suspended in water (12.5 L) and 2M sodium hydroxide solution (18.5 Kg), and solid sodium hydroxide (50 g) was added. Ethyl acetate (11.16 Kg) was added and the mixture stirred for 10 minutes until complete dissolution was achieved. Stirring was stopped and two layers separated out. The ethyl acetate layer was removed and stored. The aqueous layer was further extracted with ethyl acetate (11.16 Kg), and the combined ethyl acetate extracts were dried with magnesium sulphate (500 g), filtered and evaporated to furnish the product as a colourless semi-solid. The above process was repeated, to furnish the product in quantitative yield (9.31 Kg, 106%, contained residual ethyl acetate).

EXAMPLE 2

(+)-Bis-nefopam O,O-dibenzoyl-l-tartaric Acid Salt

The isolated product of Example 1 (7.86 Kg, 31.0 mol) was dissolved in ethanol (14.7 Kg) and stirred at room temperature. A solution of O,O-dibenzoyl-L-tartaric acid (2.75 Kg, 0.25 mol equiv.) in ethanol (16.0 Kg) was added over a period of 20 minutes. The resulting solution was allowed to stir at room temperature overnight during which time crystallisation occurred. The crystals were collected by filtration, washed with ethanol (2×2 L) and dried to constant weight at 45° C. under reduced pressure. The product was obtained as a colourless solid, 4.27 Kg, 32%. Chiral HPLC indicated 83% e.e. for (+)-nefopam.

The solid was recrystallised in two batches from ethanol (2×12.16 Kg) and the solid washed with ethyl acetate (2×2 L).

The combined solids were dried to constant weight at 45° C. under reduced pressure to furnish the product as a colourless solid, 2.90 Kg; 68%. Chiral HPLC analysis indicated 99% e.e.

Resolution concentration uses 5 volumes of ethanol with an overall 22% yield.

EXAMPLE 3

(+)-Nefopam

Sodium hydroxide (335 g, 8.38 mol, 2.5 equiv.) was dissolved in water (11.9 Kg) and the solution added to the isolated product of Example 2 (2.89 Kg, 3.34 mol). The mixture was stirred for 10 minutes and extracted with ethyl acetate (3×4.38 Kg). The ethyl acetate extracts were dried with magnesium sulphate (500 g), filtered and evaporated under reduced pressure to constant weight. The product was isolated as colourless oil, 1.53 Kg, 90%.

EXAMPLE 4

(+)-Nefopam Hydrochloride Salt

The isolated product of Example 3 (1.53 Kg) was dissolved in isopropanol (4.81 L) and the resulting solution heated to 50° C. Concentrated hydrochloric acid (498 mL) was added over 15 minutes, followed by stirring at 50° C. for 10 minutes. The solution was allowed to cool to 30° C. followed by cooling in an ice/salt bath to 0° C. (precipitation begins at 35° C.). The mixture was stirred for a further 1 hour at 0° C. The precipitate was filtered and washed with cold isopropanol (2×1.05 L) and the solid dried in a vacuum oven at 35° C. The product was obtained as a colourless solid, 1.05 Kg, 96.7% e.e.

On standing overnight, further product precipitated. The precipitate was filtered and washed with isopropanol (2×0.5 L) and dried in the vacuum oven at 35° C. The product was obtained as a colourless solid, 0.51 Kg, 99% e.e. Total yield 1.56 Kg, 89%.

EXAMPLE 5

The process of Example 2 was compared with the prior art process of Blaschke et al, supra. They may be summarised in the following Table.

TABLE

| Parameter | Known Route | New Route |
|---|---|---|
| Solvent | DMSO (4.8 volumes)/Ethanol (7 volumes) | Ethanol (5 volumes) |
| Acid | O,O-Dibenzoyl L-tartaric acid (1 molar equivalent) | O,O-Dibenzoyl L-tartaric acid (0.25 molar equivalent) |
| Salt formed | Monotartrate 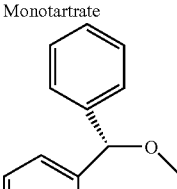 $C_{35}H_{33}NO_9$ Mol. Wt.: 611.64 | Bisnefopam tartrate (also called hemitartrate  $C_{52}H_{52}N_2O_{10}$ Mol. Wt.: 864.98 |
| Initial e.e. | 75% | 83% |
| Recrystallisation | 5 times from DMSO H$_2$O (undisclosed volume) | One time from ethanol (.4.4 volumes) |
| Final e.e. | >95% | 97% |

In summary, the literature method prepares the monotartrate salt whereas the novel method prepares the bisnefopam tartrate salt (hemitartrate). Results show that the latter has clear advantages: it is more scaleable, uses lower volumes of solvent, does not use DMSO, requires only 0.25 equivalents of resolving agent, requires only one recrystallisation, and gives a better e.e. of the final product.

The invention claimed is:

1. A process for increasing the optical purity of a mixture of enantiomers of nefopam by using a substantially single enantiomer of a O,O-diaroyltartaric acid as a resolving agent, via a bisnefopam salt of the acid.

2. The process according to claim 1, for preparing a substantially single enantiomer of nefopam by means of resolution of racemic nefopam.

3. The process according to claim 1, for preparing a substantially single enantiomer of nefopam, which comprises reverse resolution of racemic nefopam, using sequentially a single enantiomer of a O,O-dibenzoyltartaric acid and men the other enantiomer.

4. The process according to claim 1, for preparing substantially single enantiomer (+)-nefopam, which uses O,O-dibenzoyl-L-tartaric acid as the resolving agent.

5. The process according to claim 1, for preparing substantially single enantiomer (−)-nefopam, which uses O,O-dibenzoyl-D-tartaric acid as the resolving agent.

6. The process according to claim 1, which is conducted in a solvent selected from alcohols, esters, ketones and halogenated solvents.

7. The process according to claim 1, which comprises the further step of conversion of the salt obtained by the resolution to the free base form of nefopam or a pharmaceutically acceptable salt thereof.

8. The process according to claim 1, wherein the amount of the resolving agent is less than 1 equivalent.

9. The process according to claim 8, wherein said amount is no more than 0.5 equivalent.

10. A bisnefopam salt of a substantially single enantiomer of a O,O-diaroyltartaric acid.

11. The salt according to claim 10, wherein the acid is O,O-dibenzoyltartaric acid.

* * * * *

UNITED STATES PATENT AND TRADEMARK OFFICE
CERTIFICATE OF CORRECTION

PATENT NO. : 7,582,752 B2
APPLICATION NO. : 10/580621
DATED : September 1, 2009
INVENTOR(S) : Michael Christopher James Harris and Stuart Brown It is certified that error appears in the above-identified patent and that said Letters Patent is hereby corrected as shown below:

<u>Column 4, Line 63</u>
"and men" should read --and then--

Signed and Sealed this

Tenth Day of November, 2009

David J. Kappos
*Director of the United States Patent and Trademark Office*